United States Patent [19]

Paul

[11] Patent Number: 5,409,511
[45] Date of Patent: Apr. 25, 1995

[54] CENTRALIZED LASER PLUME EVACUATION SYSTEM THROUGH ARTICULATING ARMS

[75] Inventor: Gwen A. Paul, Deephaven, Minn.

[73] Assignee: Michaud, Cooley, Erickson & Associates, Inc., Minneapolis, Minn.

[21] Appl. No.: 156,458

[22] Filed: Nov. 23, 1993

Related U.S. Application Data

[63] Continuation-in-part of Ser. No. 985,823, Dec. 3, 1992, Pat. No. 5,264,026.

[51] Int. Cl.6 .......................................... B01D 35/143
[52] U.S. Cl. ........................................ 55/218; 55/274; 55/383; 55/473
[58] Field of Search ............... 55/210, 218, 274, 356, 55/383, 467, 473

[56] References Cited

U.S. PATENT DOCUMENTS

| | | | |
|---|---|---|---|
| 1,936,129 | 11/1933 | Fisk | 128/297 |
| 2,074,481 | 3/1937 | Macmullen et al. | 183/74 |
| 2,115,482 | 4/1938 | Crewe | 55/467 X |
| 2,162,019 | 6/1939 | Johnson | 98/115 |
| 3,841,145 | 10/1974 | Boubel | 73/28 |
| 3,936,284 | 2/1976 | Mason | 55/274 |
| 3,955,236 | 5/1976 | Mekelburg | 15/314 |
| 4,082,092 | 4/1978 | Foster | 128/139 |
| 4,133,658 | 1/1979 | Callewyn | 55/315 |
| 4,158,462 | 6/1979 | Coral | 285/168 |
| 4,163,650 | 8/1979 | Watson et al. | 55/126 |
| 4,199,838 | 4/1980 | Simonsson | 55/274 X |
| 4,345,342 | 8/1982 | Saito | 4/301 |
| 4,446,861 | 5/1984 | Tada | 128/139 |
| 4,503,854 | 3/1985 | Jako | 128/303.1 |
| 4,512,245 | 4/1985 | Goldman | 98/115.4 |
| 4,540,202 | 9/1985 | Amphoux et al. | 285/184 |
| 4,541,327 | 9/1985 | Lundstrom | 98/115.4 |
| 4,581,050 | 4/1986 | Krantz | 55/269 |
| 4,619,672 | 10/1986 | Robertson | 55/316 |
| 4,642,128 | 2/1987 | Solorzano | 55/217 |
| 4,685,944 | 8/1987 | Allan et al. | 55/491 |
| 4,701,193 | 10/1987 | Robertson et al. | 55/217 |
| 4,737,173 | 4/1988 | Kudirka et al. | 55/276 |
| 4,784,675 | 11/1988 | Leber et al. | 55/274 X |
| 4,786,295 | 11/1988 | Newman et al. | 55/274 X |
| 4,793,836 | 12/1988 | Griffis | 55/274 X |
| 4,810,269 | 3/1989 | Stackhouse et al. | 55/267 |
| 4,865,629 | 9/1989 | Zievers et al. | 55/97 |
| 4,905,578 | 3/1990 | Curtis et al. | 98/1.5 |
| 4,906,261 | 3/1990 | Mohajer | 55/256 |
| 4,963,134 | 10/1990 | Backscheider et al. | 604/319 |
| 4,976,694 | 12/1990 | Schreibman | 604/140 |
| 4,986,839 | 1/1991 | Wertz et al. | 55/274 |
| 5,015,243 | 5/1991 | Schifano | 604/315 |
| 5,047,072 | 9/1991 | Wertz et al. | 55/1 |
| 5,125,939 | 6/1992 | Karlsson | 55/473 X |
| 5,145,496 | 9/1992 | Mellen | 55/188 |
| 5,205,156 | 4/1993 | Asano et al. | 55/274 X |
| 5,242,474 | 9/1993 | Herbst et al. | 55/274 X |
| 5,281,246 | 1/1994 | Ray et al. | 55/356 X |

FOREIGN PATENT DOCUMENTS

WO89/11885 12/1989 WIPO .

*Primary Examiner*—Robert Spitzer
*Attorney, Agent, or Firm*—Moore & Hansen

[57] ABSTRACT

A centralized system for removing the plume resulting from laser surgery, electrocauterization or orthopaedic surgery that takes advantage of the articulating arms frequently found in medical procedure rooms. The plume is drawn away from the surgery location by a vacuum. The tubing that carries the plume is held near the location of the medical procedure, and the plume is then drawn into the tubing. The tubing leads through the articulating arm to a main located above the ceiling. The main leads to a central room that includes, in series, a centrifugal separator, a vacuum producer and a high efficiency air filter.

47 Claims, 10 Drawing Sheets

CENTRALIZED LASER PLUME EVACUATION
SYSTEM THROUGH ARTICULATING ARMS

CROSS REFERENCE TO RELATED APPLICATION

This is a continuation-in-pan of application Ser. No. 07/985,823, filed Dec. 3, 1992, now U.S. Pat. No. 5,264,026.

BACKGROUND OF THE INVENTION

1. Technical Field

The present invention relates generally to systems for the removal of airborne contaminants, such as vaporized tissue and other debris, that result from laser surgery and other surgeries that generate fumes or airborne debris.

2. Background Information

In the process of performing various forms of laser surgery, orthopaedic surgery or electrocauterization, common by-products are airborne fumes and particles, either wet or dry. For example, in the case of orthopaedic surgery, blood and debris rises from the cutting area, while in the case of laser surgery, the matter rising from the area of the operation is vaporized tissue. These by-products rise from the site of the surgery in the form of a plume, the by-products sometimes also being referred to as smoke, although they are not the result of combustion in the ordinary sense of the word. In the case of odors resulting from the lasing of organic tissue, for example, those odors are capable of lingering in the operating room for an extended time following the completion of the surgery.

Of greater concern than lingering odors, however, are the germs and viruses that may also linger in the air following the operation. These disease-carrying particles, if allowed to remain airborne in the operating room, may settle into the open wounds of the next patient being operated on, potentially resulting in the transmission of that disease to the next patient. As of the present time, it remains unclear to what extent these airborne viruses pose a threat to later patients of the operating room, although it is known that at least one virus, Human Papillomavirus DNA (HPV DNA), a wart virus, does survive the laser surgery procedure and may pose a health risk if allowed to linger in the operating room. Of potentially greater concern is the HIV virus that causes AIDS. While no conclusive evidence has yet been found that the HIV virus survives the laser surgery procedure, there is also no such evidence that it does not. Additionally, there is a risk of HIV contamination due to aerosolized blood and tissue debris, resulting from laser or orthopaedic procedures, which may remain in the air of the room where the medical procedure has been performed.

Most existing laser plume filtration systems are portable units that may be moved from operating room to operating room, as needed. They provide useful filtration features, but the treated air is recirculated back into the operating room, where microscopic particulate matter that escaped the filtration process remains for the next operating procedure. It is known to use portable units for filtration, and then exhaust the treated air outside of the operating room, but this is not commonly done because of the added inconvenience of properly configuring such a system. Further, the portable units frequently lack the system power to draw all of the airborne debris into the filtration unit in the first place.

One of the other problems with portable laser plume filtration systems of the prior art is that they frequently take up precious floor space in a busy operating room, requiring doctors and nurses to walk around them. In addition, if such a unit is placed off to the side of the room to keep it out of the way, then hoses must be connected to it leading to the patient, and the hoses then become an obstacle to contend with in the operating room. In addition, since these units are serf contained, including motorized vacuum pumps, they tend to be quite noisy, detracting from the feeling of order that is desirable in an operating room during surgery.

Manufacturers of portable units, in an effort to enhance portability and minimize size requirement, are often forced to minimize the vacuum power of the units. The effect, however, is to tend to reduce the portable unit's ability to draw all airborne particles into the filtration system, resulting in reduced effectiveness of the system.

The centralized laser plume evacuation system of the present invention overcomes difficulties described above and affords other features and advantages heretofore not available.

SUMMARY OF THE INVENTION

The centralized laser plume evacuation system of the present invention operates preferably through articulating arms in a medical procedure room, although it may also be accessed through wall or ceiling outlets or through a medical gas column. Some hospitals, for example, have three articulating arms in each operating room. These articulating arms are fastened to and suspended from the ceiling of the operating room, and provide aH medical gas services, as well as high pressure air for tool use. Electrical services within these arms include outlets and video jacks. The articulating arms are motorized and provide a range of motion, both vertically and horizontally.

The centralized laser plume evacuation system is preferably installed in an articulating arm in each procedure room. On the face of each articulating arm, there is a panel for medical gas outlets. The lower area of one panel is dedicated to providing access to the centralized laser plume evacuation system. On this panel, there is a hinged outlet to the vacuum system, as well as a user adjustable capacity control.

Evacuation takes place through flexible plastic tubing, similar to and interchangeable with the tubing used for portable systems. This tubing is available with inside diameters ranging from ⅛ inch (3.125 mm) to 1 ¼ inch (31.25 mm). A range of tubes should be stocked to allow for use for different procedures. The largest tubing will allow for the best evacuation from surface procedures. The smallest tubing is used for connection to the laparoscope. This flexible tubing is sterile and packaged for use. This tubing is then disposed of following a procedure.

The connector between the tubing and the outlet is a gasketed rigid fitting. This fitting is held into the outlet by a tooth on the hinged outlet. The intake size of this fitting varies depending on tubing size. Within this connector, there is an integral screen designed to capture any needles or sponges that may be picked up by the system.

The central components of the system include a centrifugal separator tank, garbage pump, optional disinfectant tank, vacuum producer (fan) and HEPA filter. The operating rooms are connected to the central components by a piping system that has branch takeoffs that serve all of the outlets. The piping system includes the flexible plastic tubing discussed above, as well as permanent piping. The initial part of the permanent piping system is additional flexible tubing located within the articulating arm. This tubing must be flexible to allow for movement and rotation of the arm. The inner walls of the tubing must be smooth so debris cannot build up. The flexible tubing connects into copper piping, which feeds into the main piping, all of which is located in the ceiling. All branch piping is designed with 45 degree long sweep connections into the main piping. The main piping should have long radius elbows at every 90 degree turn. Piping cleanouts should be provided at every elbow to provide access to the piping system in case of blockage. Finally, the piping system also accommodates future expansion of and connectivity to the system.

The central system components are located in a mechanical room, central to the operating rooms served by the laser plume evacuation system. The piping mains join together and are connected to the centrifugal separator tank. The tank separates debris picked up by the system from the air passing through the system. The debris, which includes vaporized tissue particles, bone dust, etc. is flushed out of the tank, through a small garbage pump, and into the sanitary sewer system. Air leaves the top of the separator tank and is drawn through the vacuum producers before entering the HEPA filter. The purpose of the filter is to capture particles before air is discharged to the outside air. The HEPA filter captures particles 0.10 microns and greater. This filter is easily removable and should be changed periodically by maintenance personnel.

It is an object of this invention to provide an efficient, convenient, easily accessible system for evacuating airborne contaminants from a hospital operating room. It is a further object of this invention to provide such a system that also exhausts the air out of the hospital operating room rather than recirculating it back into the room. It is also an object of this invention to provide such a system that is quiet, reducing any disruption that might be added to the hospital operating room brought on by loud machinery. Perhaps the most important object of this invention is to provide a laser plume evacuation system that ensures the removal of airborne germs and viruses, greatly reducing the likelihood of transmission of contagious diseases from one patient to the next.

Other objects and advantages of the invention will become apparent from the following detailed description and from the appended drawings in which like numbers have been used to describe like parts throughout the several views.

DESCRIPTION OF THE PREFERRED EMBODIMENT

Figure 1:
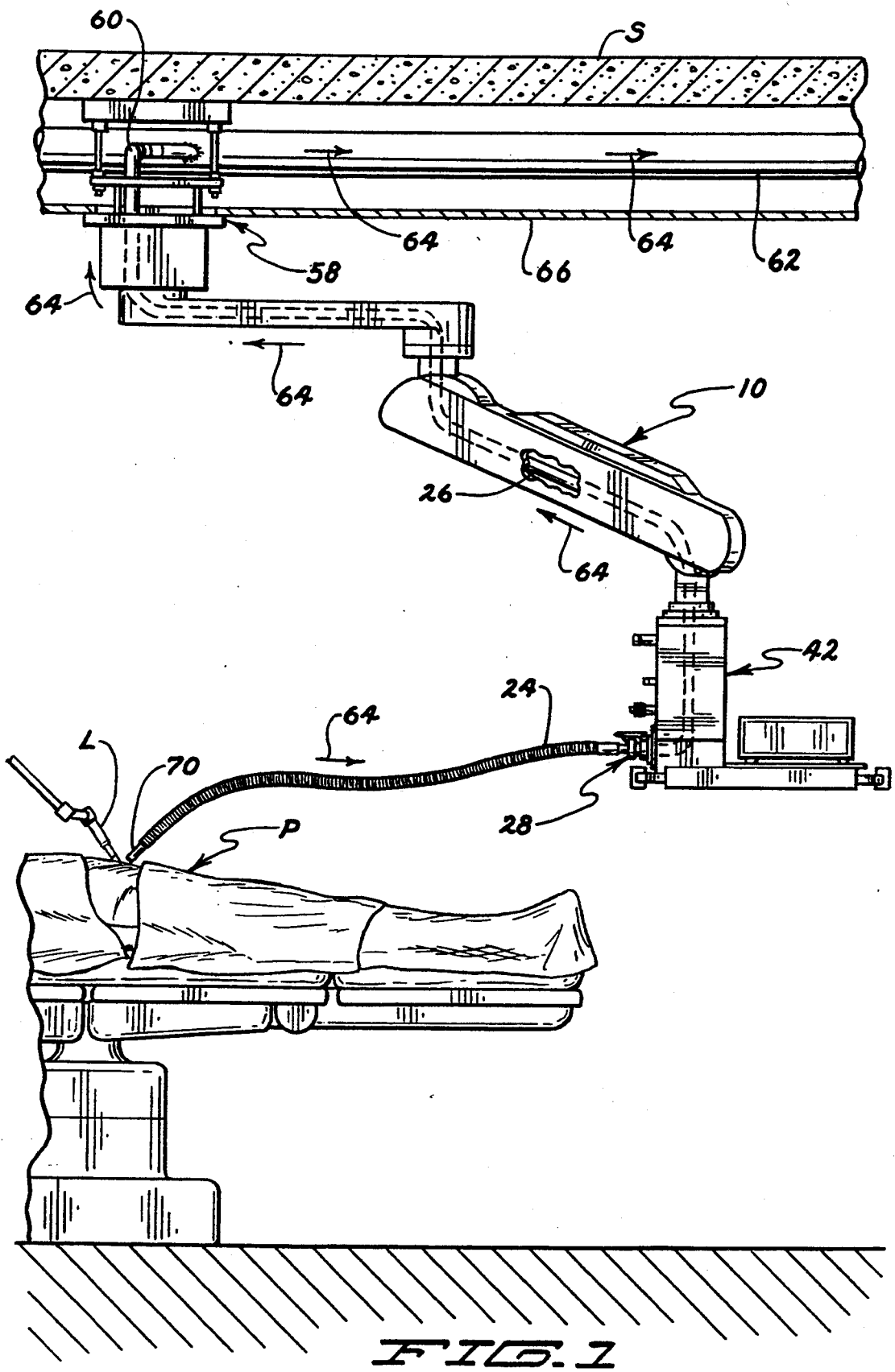
FIG. 1 shows a partially broken away view of an articulating arm in a hospital operating room, the articulating arm being equipped with and connected to flexible hose and piping of the centralized laser plume evacuation system.
Figure 2:
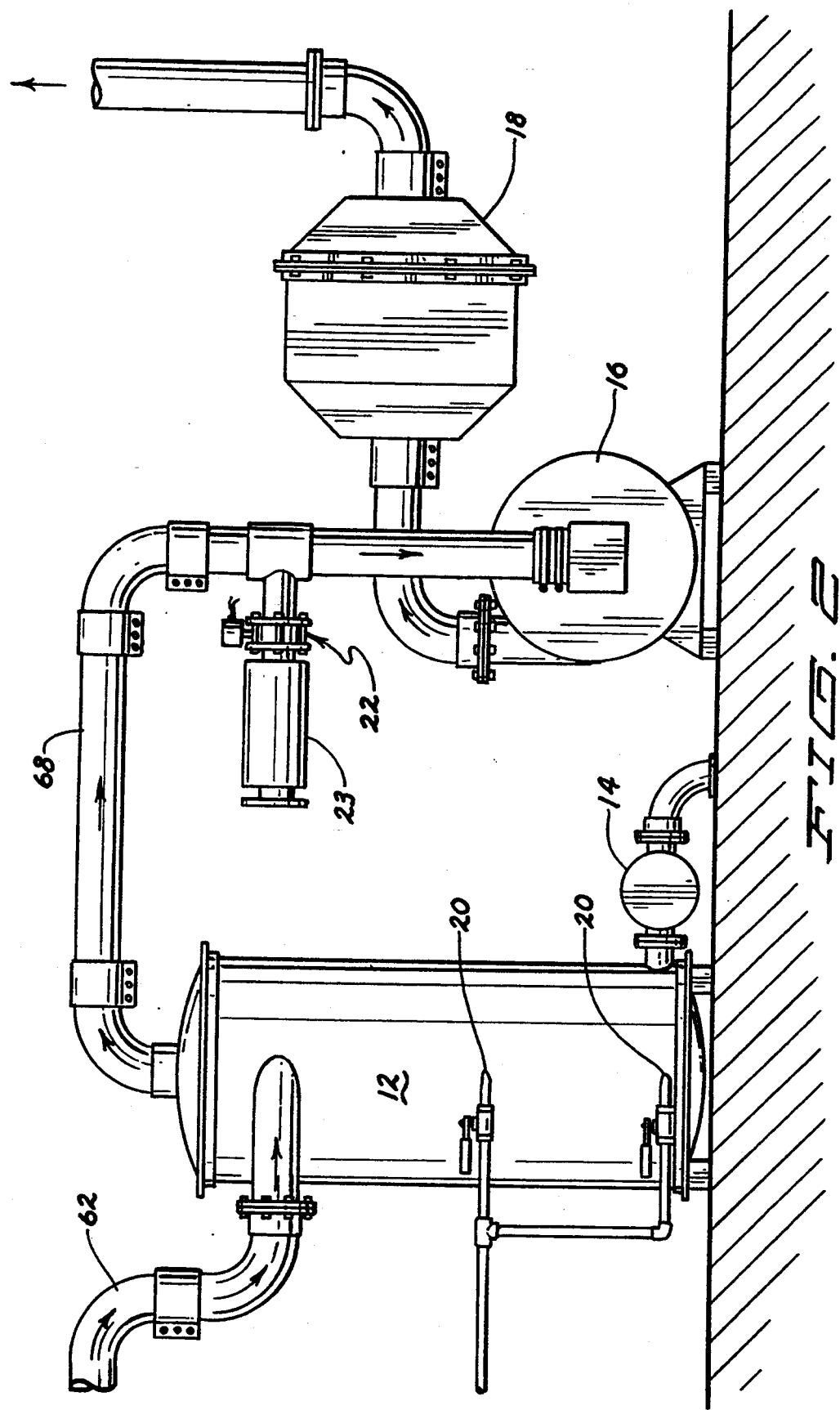
FIG. 2 shows a side view of a typical layout of a hospital mechanical room equipped with the central components of the present invention.

With reference to the drawings, and in particular to FIG. 1, the articulating arm through which the centralized laser plume evacuation system is accessed in the preferred embodiment is generally indicated by reference numeral 10. Referring to FIG. 2, the other main components of the system include a centrifugal separator tank 12, a garbage pump 14, a vacuum producer or fan 16, and a HEPA filter 18. The system may optionally include a disinfectant tank, not shown. Finally, to accommodate use of the system by varying numbers of operating rooms, bleed valve 22 is provided to permit adequate volumes of air to be drawn into the system to satisfy vacuum producer 16. A silencer 23 may also be provided to reduce the noise resulting from operation of the bleed valve.

Figure 3:
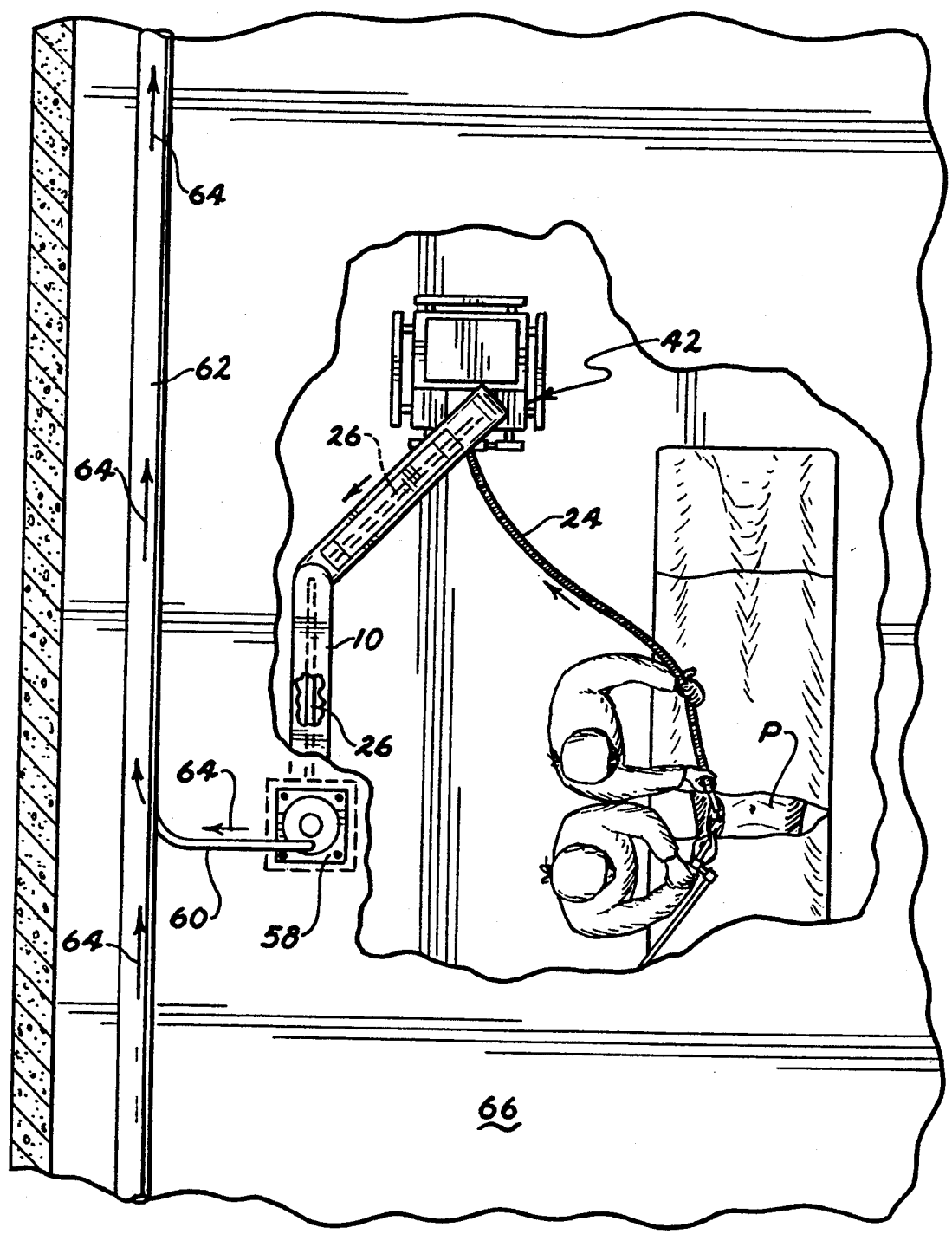
FIG. 3 shows a plan view through a broken-away portion of the ceiling of a typical hospital operating room equipped with the present invention, as it might appear in use.

Access to the system is afforded by a network of piping, beginning at the patient P with disposable flexible sterile tubing 24, as shown in FIGS. 1 and 3. Flexible sterile tubing 24, which should be disposed of after use, is available in a variety of diameters for varying procedures. For example, tubing having an inside diameter of ⅛ inch (3.125 mm) may be used for laparoscopies, while tubing having an inside diameter of 1⅛ inch (28.125 mm) may be used for removing scars or birthmarks. Extending within articulating arm 10 is smooth sided flexible tubing 26. It is important that tubing 26 have smooth sides to prevent the buildup of debris within the tubing. Tubing 26 has an inside diameter of 1¼ inch (31.25 mm) to accommodate adequately the largest size disposable tubing 24 that might be used with the system.

Figure 4:
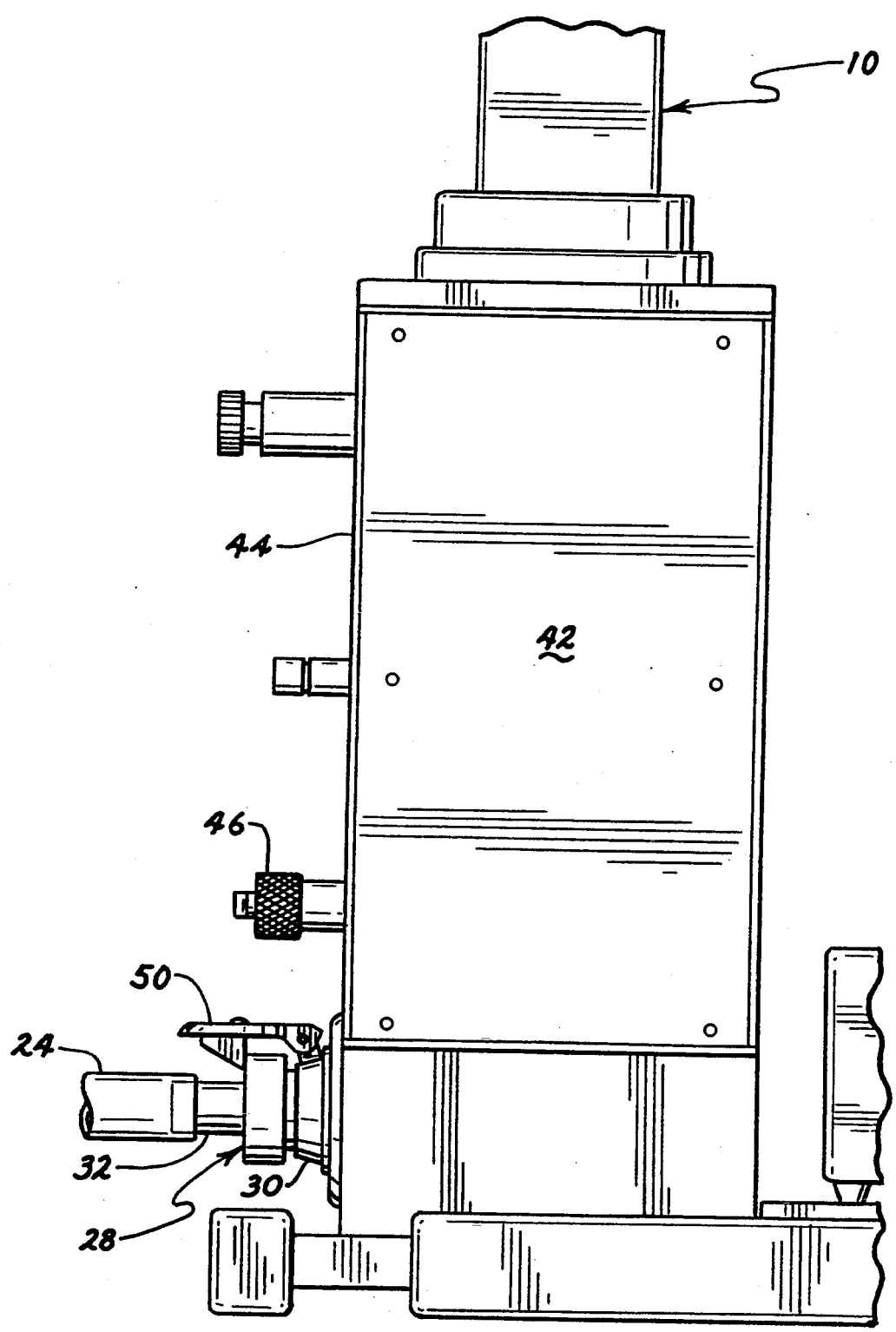
FIG. 4 shows a side view of the panel area of the articulating arm, to which is connected the disposable, flexible hose used with the present invention.
Figure 5:
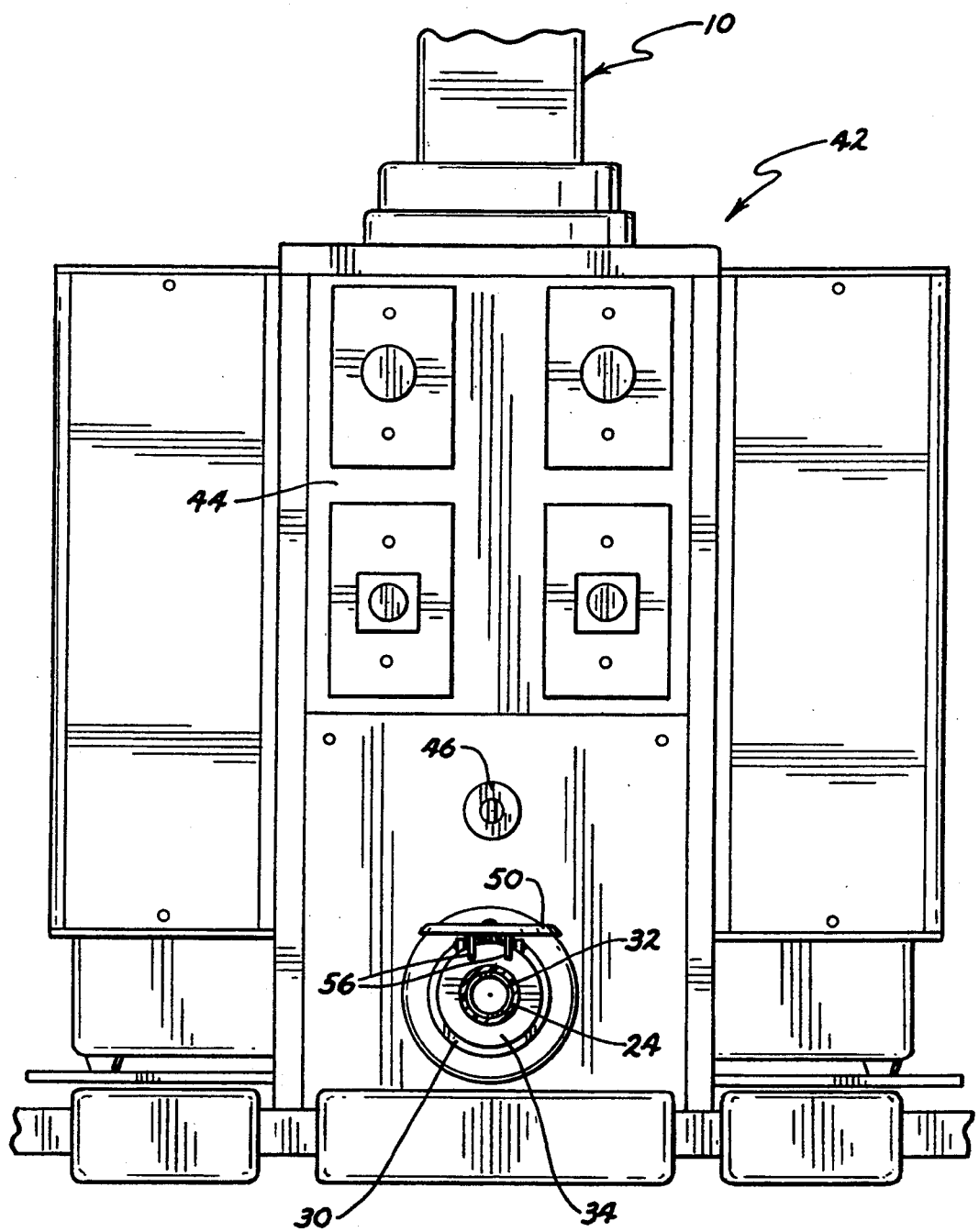
FIG. 5 shows a plan view of the control box of the articulating arm illustrated in FIG. 4.
Figure 6:
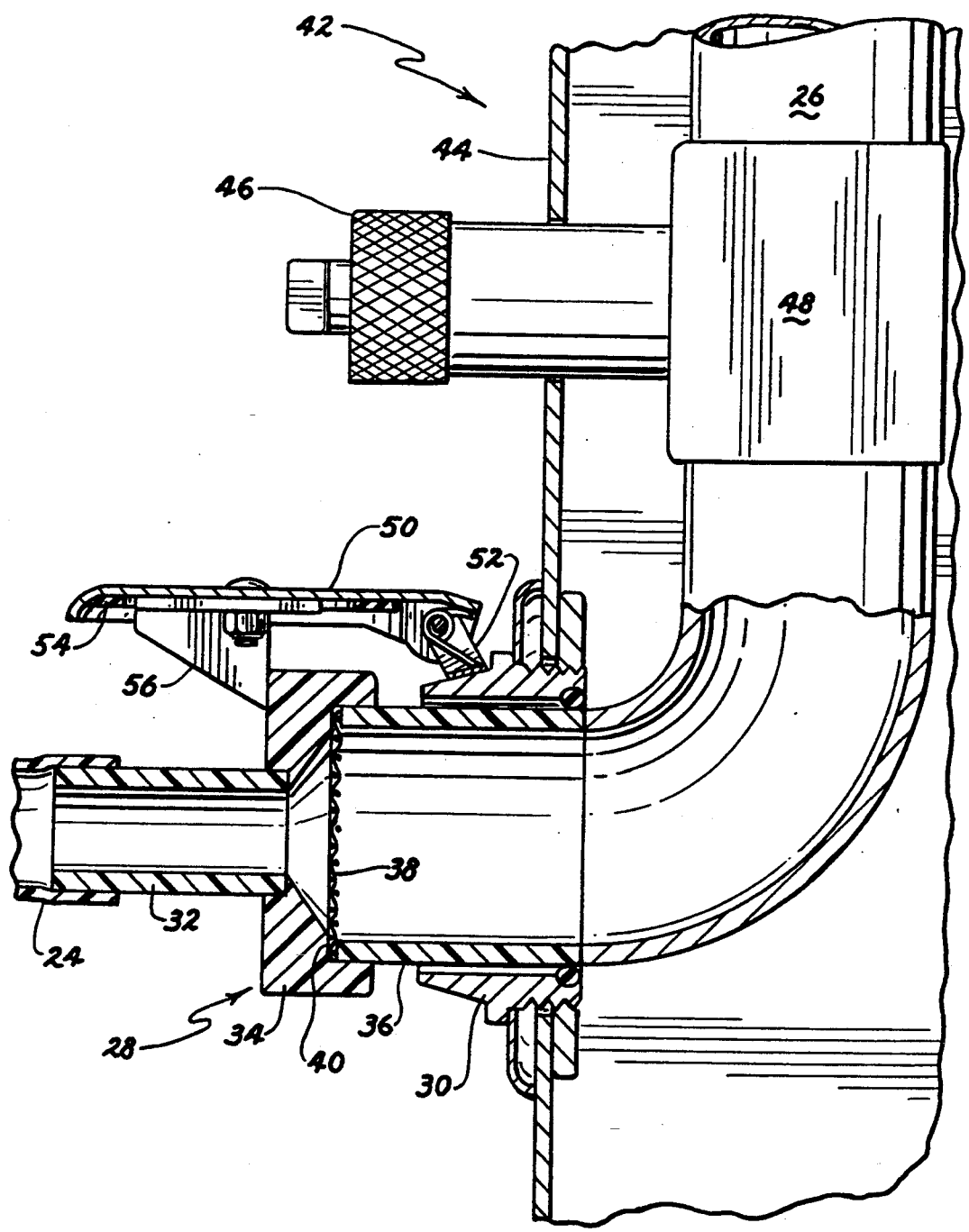
FIG. 6 is a partial section view similar to that of FIG. 4, showing the detail of the connector between the internal and external hoses of the present invention.

With particular reference to FIGS. 4–6, connection between disposable tubing 24 and smooth tubing 26 is accomplished by use of coupling assembly 28 connected as by friction fit to a connector 30. Coupling assembly 28 includes a flexible tubing engaging member 32 for engaging flexible tubing 24. Flexible tubing engaging member 32 fixedly engages tapered member 34, permitting flexible tubing 24 of reduced diameter to couple with smooth sided tubing 26. Coupling assembly 28 must include an engaging member 32 of quitable diameter to properly engage the size of flexible tubing 24 being used for the particular medical procedure being performed at the time. Thus a number of various coupling assemblies 28 need to be available providing an engaging member 32 corresponding with a different diameter of flexible tubing 24. Coupling assembly 28 also includes an arm engager 36 that slides into connector 30. As may be seen in FIG. 6, arm engager 36 bears against a screen member 38 contained within coupling assembly 28 between arm engager 36 and retaining wall segment 40 of tapered member 34. Screen member 38 is preferably approximately 1/16 inch (1.56 mm) thick, and serves to capture large items that may be drawn into flexible tubing 24 by the suction provided by the system. Such large items as sponges and needles, while they may be properly handled and disposed of by the system, must be accounted for during a surgery procedure, and it is therefore important that they be captured by screen member 38 so that a count may be made of them at the end of the procedure. The tubing engaging member 32, tapered member 34, arm engager 36 and screen member 38 of coupling assembly 28 may be made of molded plastic or stainless steel. If made of plastic, these components may be injection molded as one piece, with a steel or plastic screen captured therein, or they may be molded separately and assembled together to form a unit.

FIGS. 4 and 5 illustrate views of a typical control box 42 of an articulating arm 10, which, as may be seen in FIGS. 1 and 3, is located at the end of the articulating arm, and includes a control panel 44. FIG. 5 shows on the upper part of control panel 44 a typical arrangement of controls and nozzles, which may connect to pressurized gas lines containing $CO_2$ or $O_2$, or may include video input connections or access to other supplies or services routinely necessary for surgery procedures. The lower part of control panel 44 may typically appear similar to the upper portion, as illustrated in FIG. 5, but the present invention requires the use of at least an entire half of the control panel. For embodiments of the system that do not include articulating arm 10, control panel 44 may be attached to a wall or ceiling of the procedure room or to a medical gas column.

Also illustrated in FIGS. 4-6 is a control knob 46 for controlling the vacuum of the centralized laser plume evacuation system. The vacuum is infinitely variable between zero and eighty to ninety CFM (cubic feet per minute). Lower settings of approximately ten CFM are preferable for procedures such as laparoscopies that require smaller diameter hoses, since these procedures generally create a smaller plume and because the flexible tubing 24 used with this procedure is quite small in diameter, and larger vacuums tend to cause the hose to collapse. Higher settings of approximately eighty CFM are required for procedures such as removing scars or birthmarks, when flexible tubing 24 of larger diameter is used. As shown in FIG. 6, control knob 46 controls a standard ball valve 48 that controls the vacuum passing through smooth side flexible tubing 26 that passes through articulating arm 10.

Connector 30, when not in use, is covered by connector cover 50, which is biased toward the covering position by a spring 52. A round gasket 54, preferably of rubber, is included on the inner surface of connector cover 50, to seal the connector when not in use. It is important to include a gasket 54 to prevent air from leaking into the system since the vacuum producer 16 may be overworked and its reliability and efficiency reduced if air was permitted to leak into the system from connectors 30 of articulating arms 10 in operating rooms where the laser plume evacuation system was not in use. Connector cover 50 also includes at least one coupling retaining tooth 56, shown in FIGS. 5 and 6. Coupling retaining teeth 56 engage tapered member 34 of coupling assembly 28, as shown in FIG. 6, thereby retaining coupling assembly 28 in firm engaged relationship with connector 30.

With reference to FIGS. 1 and 3, the continuation of the piping system from the hospital operating room is illustrated, showing smooth sided flexible tubing 26 passing through articulating arm 10 and then through a ceiling mounting assembly 58 and connecting to branch 60, which in turn connects as by welding to main 62. It is important that aH welded connections satisfy standards set for medical vacuum systems. The direction of air flow passing through the system is indicated by direction arrows 64. Branch 60 is preferably approximately 1¼ inch (31.25 mm) in diameter, and main 62 is preferably approximately six inches (150 mm) in diameter. Ceiling mounting assembly 58 is anchored to structural ceiling S, and main 62 is positioned between structural ceiling S and finished ceiling 66.

As illustrated in FIG. 2, centrifugal separator 12, vacuum producer 16 and HEPA filter 18 are preferably located in a single room such as a room containing other mechanical controls and assemblies, each device being easily accessible for maintenance and repair. Main 62 enters the room and feeds first into centrifugal separator 12. Centrifugal separator 12 forces air introduced therein to spin rapidly about the periphery of the tank, separating solid and liquid wastes from the gases introduced from main 62. The surviving gases leave centrifugal separator 12 through an opening in the top thereof, and enter secondary main 68. All solid and liquid wastes separated from the air introduced into centrifugal separator 12 are expelled from the tank into the sewage system by means of garbage pump 14. Before being discharged, however, the wastes are treated by a disinfectant solution. Centrifugal separator 12 may also be rinsed periodically by non-foaming disinfectant solutions. These disinfectant solutions are introduced into centrifugal separator 12 through disinfectant inlets 20. As shown in FIG. 2, there may be two such disinfectant inlets 20. The upper one permits of rinsing the centrifugal separator portion of the tank, while the lower one permits of disinfection of the contents at the bottom of the separator 12 that have been separated from the air passing through the tank.

Air is drawn through the system by vacuum producer 16, which may be simply a large fan. In a hospital setting where several operating rooms are provided with the plume evacuation system, for example, a twenty-five horsepower vacuum producer may provide adequate vacuum to power the system. Although FIG. 2 shows only one such vacuum producer 16, in an actual hospital setting it is advisable to include at least two such fans to ensure redundancy in case one of the fans fails. Further, an unlimited number of vacuum producers 16 may be provided in series to provide adequate vacuum to service a system of virtually any size. It is important to locate vacuum producer 16 after centrifugal separator 12 because the contaminants that are removed from the air stream by centrifugal separator 12 could have an adverse effect on vacuum producer 16 if not removed from the air first. To prevent damage to vacuum producer 16 or inefficient operation of the system, bleed valve 22 is provided on secondary main 68. Upon detecting that vacuum producer 16 is operating inefficiently or is in danger of being damaged due to insufficient air flow, bleed valve 22 will permit additional air to be introduced into secondary main 68. This condition might arise, for example, where many inlets are provided throughout a system, but none or only a few are being used, and little or no air is therefore entering the system from the inlets at each articulating arm 10.

Before being exhausted out of the hospital, the air in secondary main 68 passes through HEPA filter 18, which provides filtration that is approximately 99.9995% efficient. The preferred filters for this system are Guide Pack falters manufactured by American Air Filter Co. In an alternate embodiment, HEPA filter 18 may be replaced by an incinerator, which would be located outside of the hospital. The incinerator simply provides an alternative means for destroying any particulates or other contaminants remaining in the air after passing through centrifugal separator 12. Another alternative would be to use an active filtration member, such as those manufactured by EnviroSurgical, Inc., which includes a foaming solution introduced into the filter that neutralizes the residue exhausted from the medical procedure room.

Figure 7:
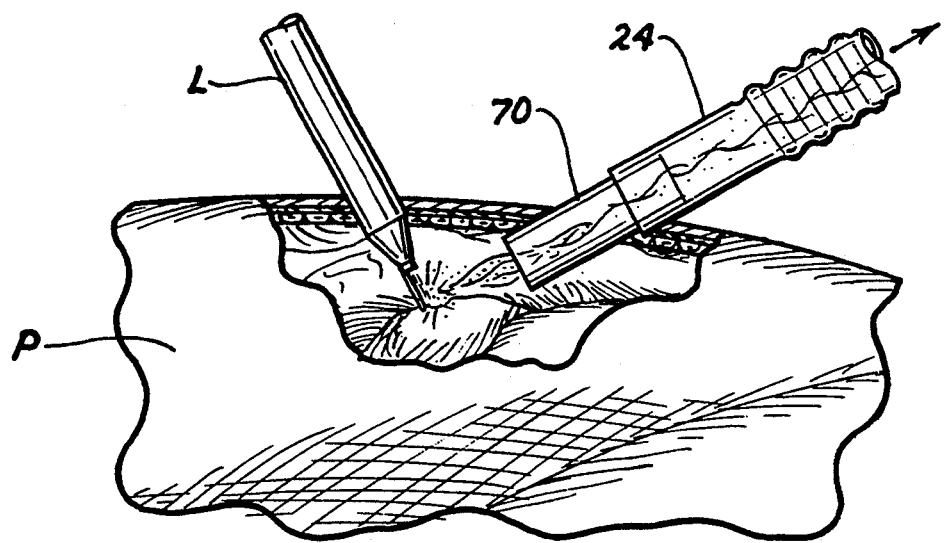
FIG. 7 shows a perspective view of the external hose of the present invention as it appears in a typical operating procedure.
Figure 8:
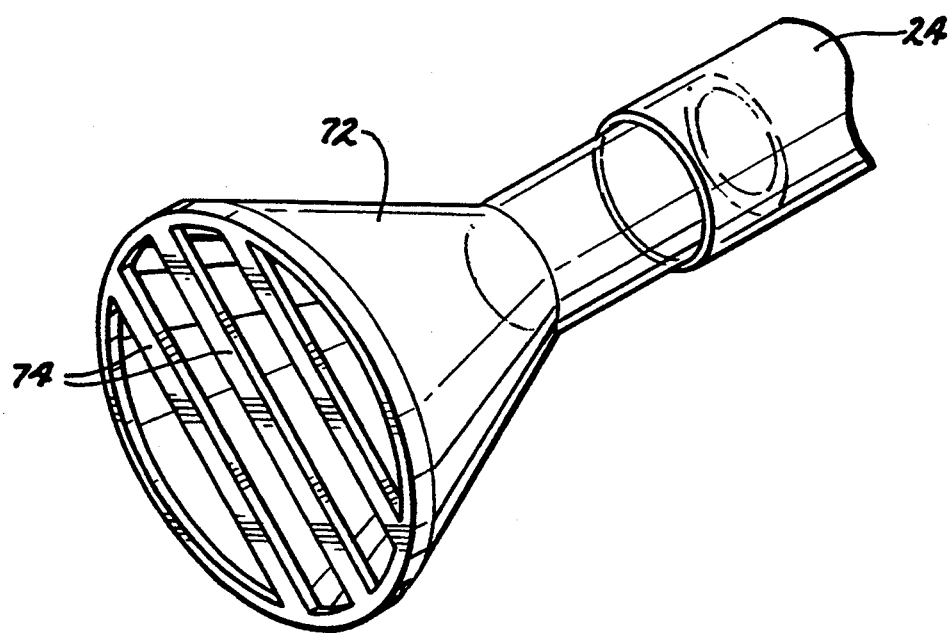
FIG. 8 shows a funnel adaptor usable with the plume-receiving end of the external hose of the present invention.

FIG. 7 illustrates an application of the laser plume evacuation system. While patient P is being operated on using laser wand L held by the surgeon, disposable flexible tubing 24, which may have an adaptor 70 attached to the inlet end thereof, is held in position by a nurse or other attendant during the operating procedure. Adaptor 70, which has walls that are more rigid than those of flexible tubing 24, slides into the end of flexible tubing 24, to help maintain a uniform opening at the end of the tube, where there is otherwise a tendency for tubing 24 to collapse due to the suction of the plume evacuation system. The adaptor may take the form of funnel shaped expander 72 illustrated in FIG. 8. Expander 72 includes at least one slot formed by strips 74 to regulate the amount of air entering expander 72, maintaining the level of the suction by diminishing the surface area.

Figure 10:
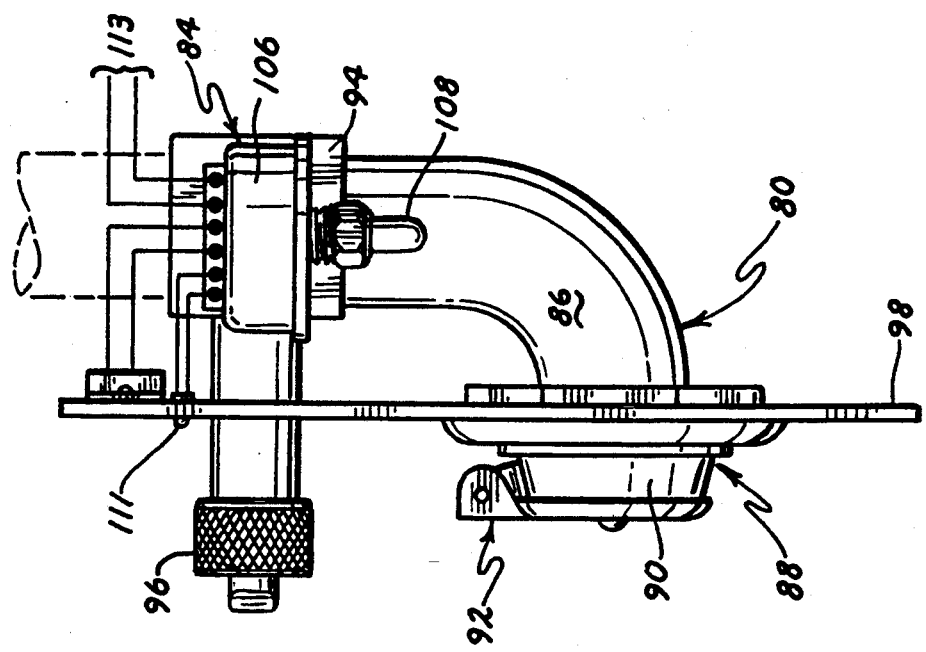
FIG. 10 shows a side view of the display and alarm panel module.
Figure 9:
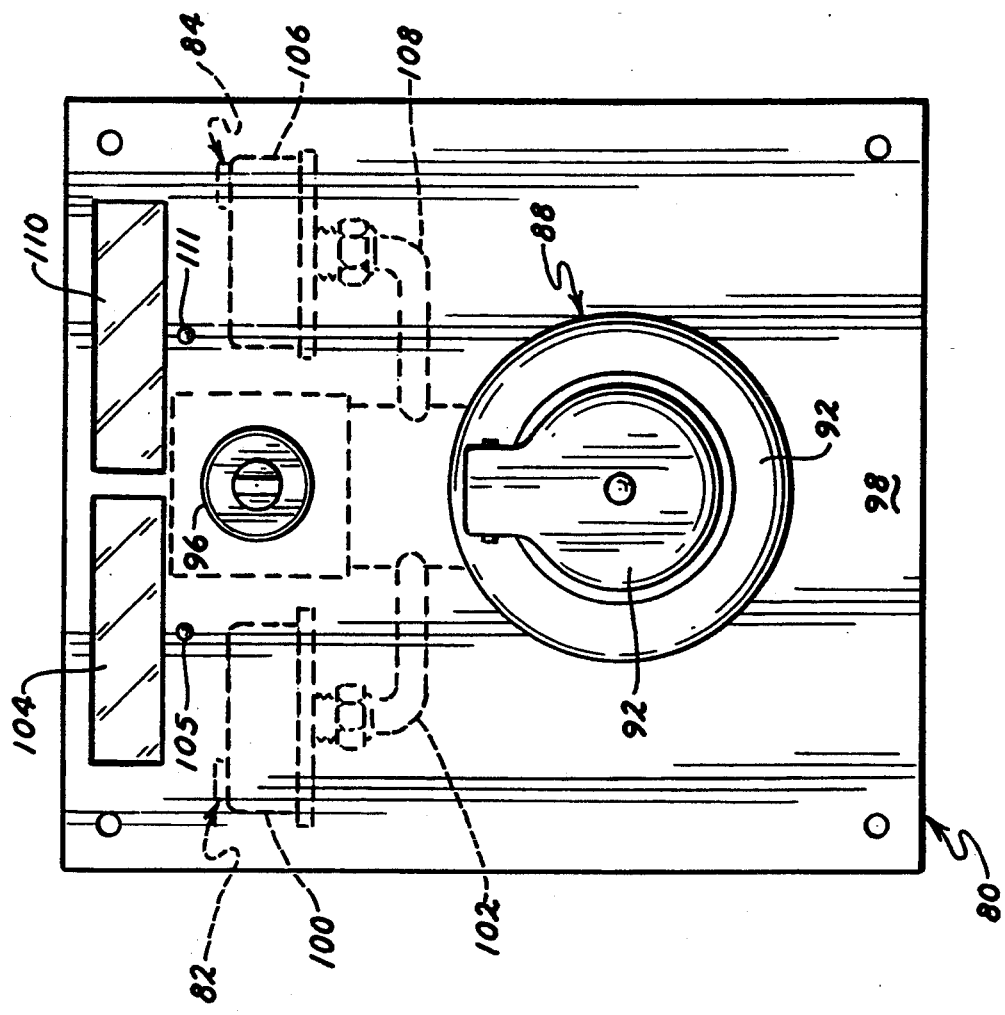
FIG. 9 shows a plan view of the display and alarm panel module.

FIGS. 9 and 10 illustrate a display and alarm panel module 80, that includes pressure sensing assembly 82 and flow sensing assembly 84. Display and alarm panel module 80 furnishes a self-contained unit that may be plugged in directly to control box 42 of articulating arm 10, for example. Also provided is a preferably rigid elbow 86 attached on one end to a connector assembly 88, including a connector 90 and a connector cover assembly 92, and attached on the other end to a valve assembly 94. Valve assembly 94 includes a valve control knob 96 projecting from mounting panel 98 of display panel module 80. Pressure sensing assembly 82 includes a pressure sensor 100 connected to elbow 86 via tube 102 to determine the air pressure at the outlet of display panel module 80. The measurement made by pressure sensor 100 is digitally displayed on display 104, which is preferably a light emitting diode (LED). In the event that air pressure as measured by pressure sensor 100 drops below a predetermined value, a small red LED 105 is illuminated by pressure sensing assembly 82 as an alarm or notification to the operating room personnel. Additionally, the status of the air flow at connector 90, including the presence of an alarm condition triggered by pressure sensing assembly 82, may optionally notify a central automated building control system via a line output (not shown) carrying an electrical or pneumatic signal indicating that the vacuum generated by vacuum producer 16 should be increased. Flow sensing assembly 84 includes a flow sensing device 106 connected to elbow 86 via tube 108 to determine the flow velocity at the outlet of display panel module 80. The measurement made by flow sensing device 106 is digitally displayed on display 110, which preferably also is a LED. In the event that air flow as measured by pressure flow sensing device 106 drops below a predetermined value, a small red LED 111 is illuminated by flow sensing assembly 84 as an alarm or notification to the operating room personnel. Additionally, the status of the air flow at connector 90, including the presence of an alarm condition triggered by flow sensing assembly 84, may optionally notify a central automated building control system via line output 113 carrying an electrical or pneumatic signal indicating that the vacuum generated by vacuum producer 16 should be increased. It is important that tubes 102, 108 of pressure sensing assembly 82 and flow sensing assembly 84, respectively, intersect elbow 86 at a point between valve assembly 94 and connector assembly 88. Display panel module 80 may include only pressure sensing assembly 82 or flow sensing assembly 84, but preferably includes both.

Additionally, sensing ports, commonly referred to as "Pete's plugs" (not shown), are preferably supplied at periodic intervals throughout the centralized laser plume evacuation system, especially in main 62, but also in branches 60. These sensing ports permit of the temporary introduction of air pressure sensors for system testing, without running the risk of fouling the sensors from the liquids that may pass through the system.

Figure 11:
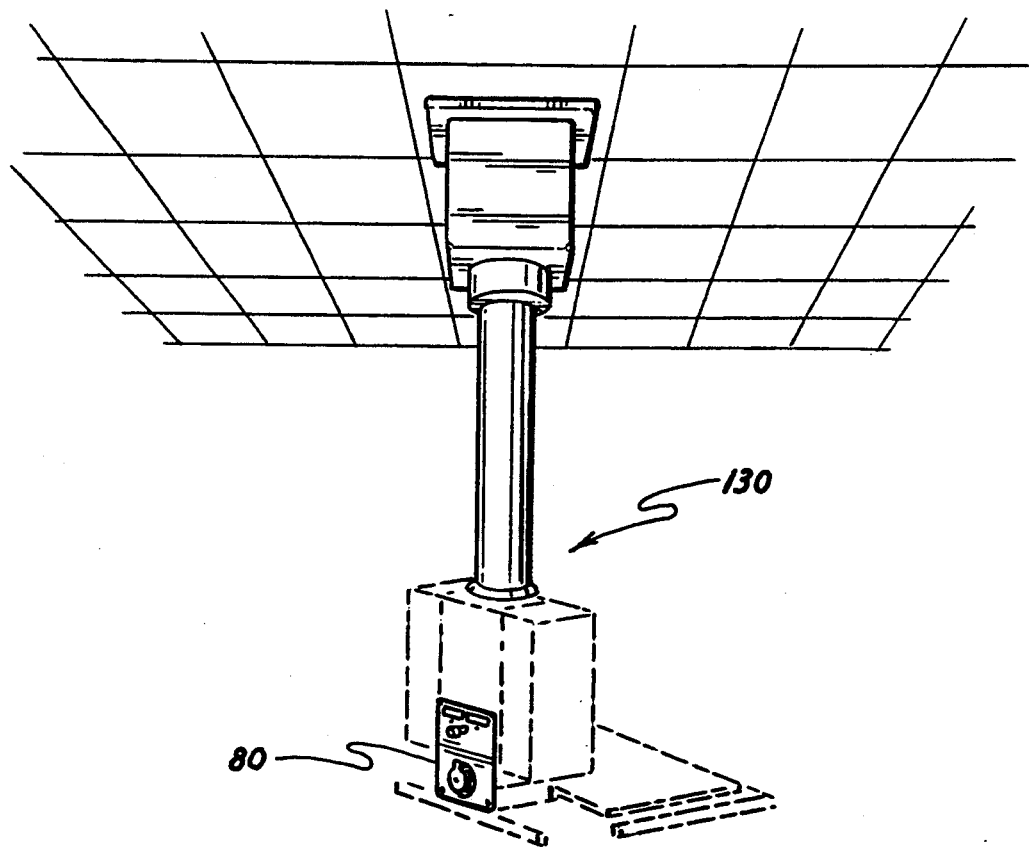
FIG. 11 shows a perspective view of a medical gas column with a display and alarm panel module in a medical procedure room.
Figure 12:
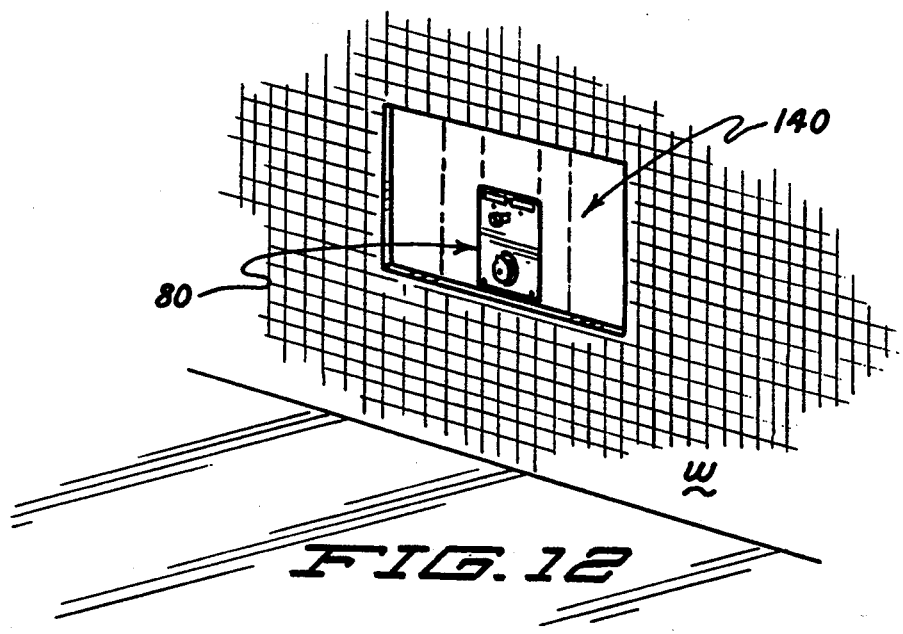
FIG. 12 shows a perspective view of wall mounted display and alarm panel module in a medical procedure room.

FIG. 11 illustrates a fixed medical gas column 130 including display and alarm panel module 80, and FIG. 12 illustrates a wall panel 140, also including display and alarm panel module 80. Wall panel 140 is installed on wall W of the medical procedure room. Alarm panel 80 may also be installed directly to wall W. These alternative embodiments each include the same internal elements, such as tubing 26 and main 62, or their equivalents, as the embodiment illustrated in FIGS. 1-10. These alternative embodiments are illustrated to demonstrate two possible additional fixtures in which display and alarm panel module 80 may be installed.

Figure 14:
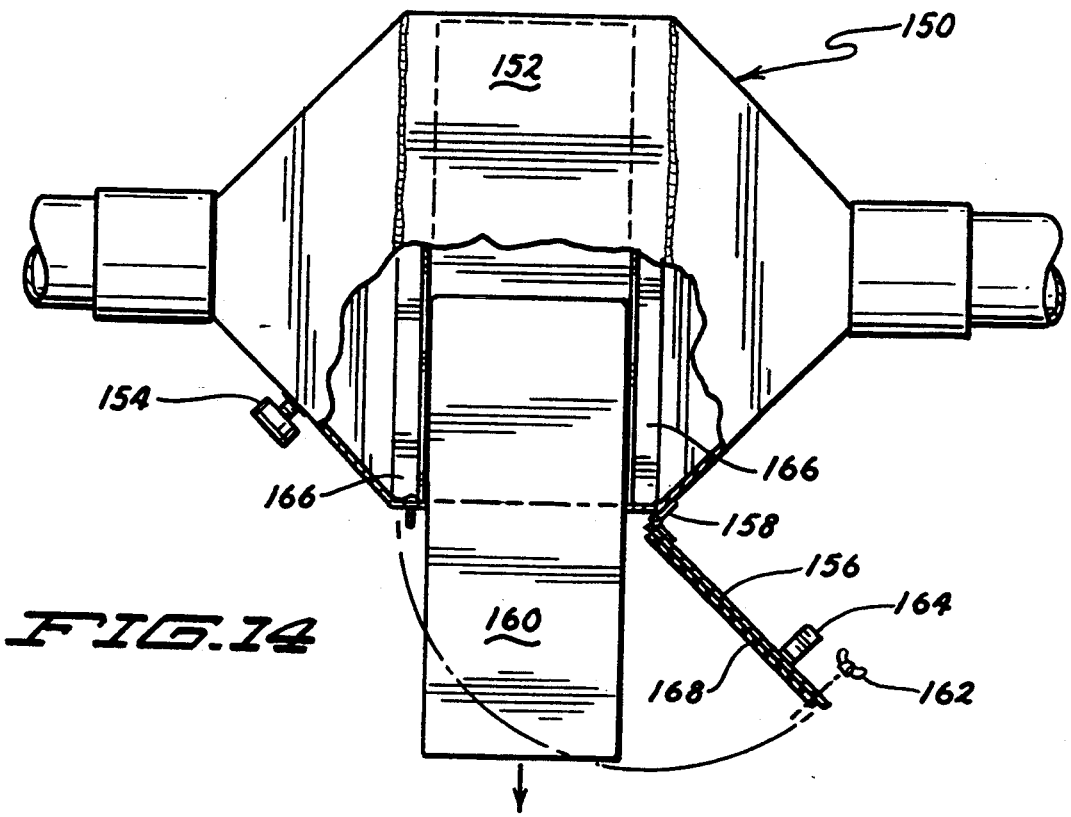
FIG. 14 shows a top plan view of the modified version of the filter assembly with the filter element extending therefrom.
Figure 13:
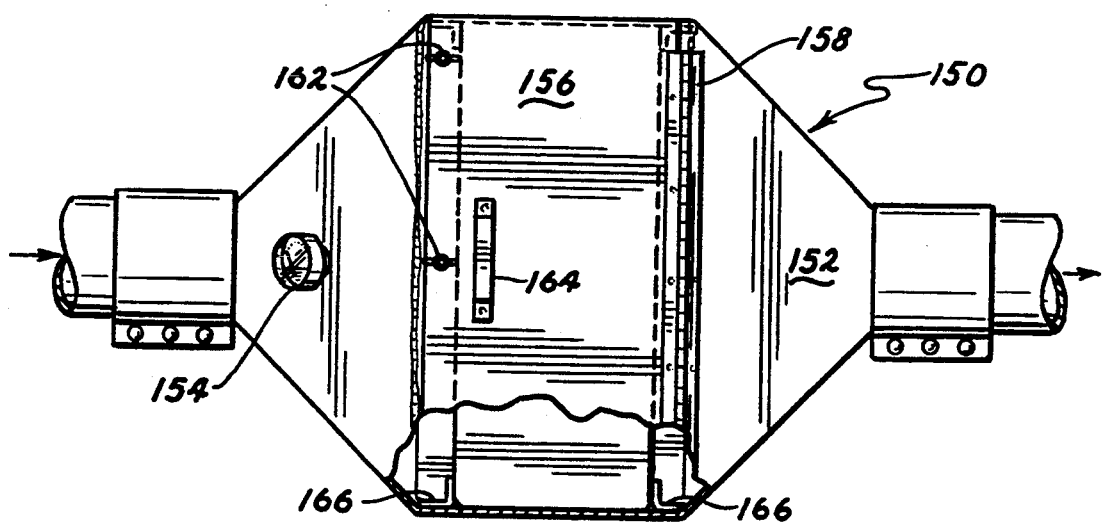
FIG. 13 shows a partially broken away side elevation of a modified version of the filter assembly.

FIGS. 13 and 14 illustrate a modified filter assembly 150, including housing 152, differential pressure gauge 154, and access door 156 mounted to housing 152 with piano hinge 158 extending along the length of access door 156. Pressure gauge 154 indicates the air pressure drop across falter element 160, which may be either a HEPA filter, a treated falter, or some other high efficiency filter member, depending on the preference of the user of the system. Once the pressure drop indicated by pressure gauge 154 reaches a predetermined value, this is an indication that filter element 160 needs to be replaced. To replace falter element 160, wing nuts 162 are loosened and removed, and access door 156 is pulled open with handle 164, access door 156 pivoting along hinge 158. Lengths of angle iron 166 form a track within which filter dement 160 may be slidably removed and inserted. After replacing filter element 160, the above steps are reversed. It is important to note that access door 156 includes a rubber gasket 168 about its inner periphery to provide an airtight seal with housing 152.

In use, flexible tubing 24 is attached to coupling assembly 28, which is plugged into connector 30 on control panel 44 of articulating arm 10. Articulating arm 10 is positioned to be conveniently located relative to the area of patient P on which the procedure is to be performed. Connector cover 50 is positioned so that coupling retaining teeth 56 engage tapered member 34 of coupling assembly 28. Control knob 46 is adjusted to provide the appropriate level of vacuum for the procedure about to be performed. Next, the inlet end of flexible tubing 24, including adaptor 70, is held in position by an attendant within approximately two inches (50 mm) of the site of the medical procedure. While the procedure is being performed, flexible tubing 24 continues to be held in position. As the plume of airborne contaminants rises from the site of the medical procedure, the plume is drawn into flexible tubing 24, through which it passes to smooth sided flexible tubing 26, branch 60 and main 62. All airborne contaminants are thus drawn out of and away from the operating room. These airborne contaminants may also include trace or waste gases present in the operating room during a surgery, such as anesthesia that escapes from around the patient's mask. Such gases are generally detectable by their odor, and the inlet end of flexible tubing 24 may simply be moved to the location of the odor—i.e., near the patient's mask—to exhaust the gas from the operating room.

The plume of airborne contaminants may also include electrocautery debris generated during electrosurgical procedures. Such procedures, including wart removal, use an electrosurgical generator, and result in the burning of tissue, rather than its vaporization, as from laser procedures. Additionally, the airborne contaminants referred to above may include bone dust resulting from orthopaedic procedures.

After leaving the operating room, the airborne contaminants are drawn into the centrifugal separator 12. There, the solid and liquid contaminants are separated out of the air, and gather at the bottom of the tank that comprises the housing of centrifugal separator 12. These solid and liquid contaminants may be treated by a non-foaming neutralizing solution introduced into the tank through disinfectant inlets 20 before being discharged from the tank by garbage pump 14. The air leaving centrifugal separator 12 is exhausted into secondary main 68, drawn through vacuum producer 16 and forced through high efficiency filter 18 before being exhausted to the atmosphere outside of the building housing the medical procedure rooms.

It is also important to thoroughly clean the centralized laser plume evacuation system on a periodic basis to rinse residual debris and bacteria that may build up on the inside of tubing 26, branch 60 or main 62. This cleaning may be accomplished by drawing a non-foaming neutralizing solution through the inlet end of disposable flexible tubing 24. The non-foaming neutralizing solution may, for example, be drawn from a pan or basin in the medical procedure room. It is preferable, however, to provide a disposable container (not shown) attachable to disposable flexible tubing 24, from which the neutralizing solution may be drawn directly. The neutralizing solution will then be discharged from the system in the same fashion as other liquids drawn into the system during ordinary usage. The use of such a rinsing system on a regular basis should minimize system maintenance over the life of the centralized laser plume evacuation system.

While the preferred embodiments of the invention have been described, it should be understood that various changes, adaptations and modifications may be made therein without departing from the spirit of the invention and the scope of the appended claims.

What is claimed is:

1. A modular display and connection unit for use with a centralized system for removing airborne contaminants from the site of at least one medical procedure being performed in at least one of a plurality of medical procedure rooms connected to the centralized system, the airborne contaminants being the result of the medical procedures performed in the medical procedure rooms, the centralized system including piping means for transporting the airborne contaminants from the medical procedure room, the modular display and connection unit comprising:
    a panel member having a front side and a rear side, said panel member being mountable to a support assembly providing access to the centralized system for removing airborne contaminants;
    an access outlet integral with said panel member, said access outlet providing access to the centralized system for removing airborne contaminants;
    means for connecting said access outlet to the piping means of the centralized system for removing airborne contaminants; and
    means for sensing the pressure of air passing through the modular display and connection unit.

2. The modular display and connection unit described in claim 1, further comprising:
    display means operatively connected to said air pressure sensing means for displaying the pressure of air passing through the modular display and connection unit as detected by said air pressure sensing means, said display means being mountable on said front side of said panel member.

3. The modular display and connection unit described in claim 1, wherein said means for connecting said access outlet to the piping means of the centralized system comprises:
    a rigid pipe member having a first end and a second end, said first end of said rigid pipe member being affixed to and extending from said access outlet on said rear side of said panel member.

4. The modular display and connection unit described in claim 3, wherein said means for sensing the pressure of air passing through the modular display and connection unit comprises:
    a pressure sensor; and
    a tube member permitting fluid communication between said pressure sensor and said rigid pipe member.

5. The modular display and connection unit described in claim 4, further comprising:
    a flow control valve intersecting and communicating with said second end of said rigid pipe member; and
    a manually actable valve control knob for controlling said flow control valve, said valve control knob projecting from said front side of said panel member.

6. The modular display and connection unit described in claim 5, further comprising:
    alarm means mounted to said panel member and operatively connected to said pressure sensor.

7. The modular display and connection unit described in claim 6, wherein said alarm means comprises:
  means for visually indicating an alarm condition mounted on said front side of said panel member, said means for visually indicating an alarm condition being actuated by a drop in pressure as indicated by said pressure sensor.

8. The modular display and connection unit described in claim 7, wherein said means for visually indicating an alarm condition comprises:
  a light emitting diode.

9. The modular display and connection unit described in claim 8, further comprising:
  display means operatively connected to said pressure sensor for displaying the pressure of air passing through the modular display and connection unit as detected by said pressure sensor, said display means being mountable on said front side of said panel member.

10. The modular display and connection unit described in claim 1, further comprising:
  alarm means mounted to said panel member and operatively connected to said air pressure sensing means.

11. The modular display and connection unit described in claim 10, wherein said alarm means comprises:
  means for visually indicating an alarm condition, said means for visually indicating an alarm condition being actuated by a drop in pressure as indicated by said air pressure sensing means.

12. The modular display and connection unit described in claim 1, further comprising:
  means for sensing the velocity of air flow through the modular display and connection unit.

13. The modular display and connection unit described in claim 12, wherein said means for connecting said access outlet to the piping means of the centralized system comprises:
  a rigid pipe member having a first end and a second end, said first end of said rigid pipe member being affixed to and extending from said access outlet on said rear side of said panel member.

14. The modular display and connection unit described in claim 13, wherein said means for sensing the velocity of air flow through the modular display and connection unit comprises:
  a flow velocity sensor; and
  a tube member permitting fluid communication between said flow velocity sensor and said rigid pipe member.

15. The modular display and connection unit described in claim 14, further comprising:
  a flow control valve intersecting and communicating with said second end of said rigid pipe member; and
  a manually actuable valve control knob for controlling said flow control valve, said valve control knob projecting from said front side of said panel member.

16. The modular display and connection unit described in claim 15, further comprising:
  first alarm means mounted to said panel member and operatively connected to said air pressure sensing means.

17. The modular display and connection unit described in claim 16, wherein said first alarm means comprises:
  first means for visually indicating an alarm condition, said first means for visually indicating an alarm condition being actuated by a drop in pressure as indicated by said air pressure sensing means.

18. The modular display and connection unit described in claim 17, wherein said first means for visually indicating an alarm condition comprises:
  a first light emitting diode.

19. The modular display and connection unit described in claim 18, further comprising:
  second alarm means mounted to said panel member and operatively connected to said flow velocity sensor.

20. The modular display and connection unit described in claim 19, wherein said second alarm means comprises:
  second means for visually indicating an alarm condition, said second means for visually indicating an alarm condition being actuated by a drop in air flow velocity as indicated by said flow velocity sensor.

21. The modular display and connection unit described in claim 20, wherein said second means for visually indicating an alarm condition comprises:
  a second light emitting diode.

22. The modular display and connection unit described in claim 21, further comprising:
  first display means operatively connected to said air pressure sensing means for displaying the pressure of air passing through the modular display and connection unit as detected by said air pressure sensing means, said first display means being mountable on said front side of said panel member.

23. The modular display and connection unit described in claim 22, further comprising:
  second display means operatively connected to said flow velocity sensor for displaying the air flow velocity of air passing through the modular display and connection unit as detected by said flow velocity sensor, said second display means being mountable on said front side of said panel member.

24. A modular display and connection unit for use with a centralized system for removing airborne contaminants from the site of at least one medical procedure being performed in at least one of a plurality of medical procedure rooms connected to the centralized system, the airborne contaminants being the result of the medical procedures performed in the medical procedure rooms, the centralized system including piping means for transporting the airborne contaminants from the medical procedure room, the modular display and connection unit comprising:
  a panel member having a front side and a rear side, said panel member being mountable to a support assembly providing access to the centralized system for removing airborne contaminants;
  an access outlet integral with said panel member, said access outlet providing access to the centralized system for removing airborne contaminants;
  means for connecting said access outlet to the piping means of the centralized system for removing airborne contaminants; and
  means for sensing the velocity of air flow through the modular display and connection unit.

25. The modular display and connection unit described in claim 24, further comprising:
  display means operatively connected to said air flow velocity sensing means for displaying the velocity of air flow through the modular display and connection unit as detected by said air flow velocity sensing means, said display means being mountable on said front side of said panel member.

26. The modular display and connection unit described in claim 24, wherein said means for connecting said access outlet to the piping means of the centralized system comprises:
 a rigid pipe member having a first end and a second end, said first end of said rigid pipe member being affixed to and extending from said access outlet on said rear side of said panel member.

27. The modular display and connection unit described in claim 26, wherein said means for sensing the velocity of air flow through the modular display and connection unit comprises:
 a flow velocity sensor; and
 a tube member permitting fluid communication between said flow velocity sensor and said rigid pipe member.

28. The modular display and connection unit described in claim 27, further comprising:
 a flow control valve intersecting and communicating with said second end of said rigid pipe member; and
 a manually actuable valve control knob for controlling said flow control valve, said valve control knob projecting from said front side of said panel member.

29. The modular display and connection unit described in claim 28, further comprising:
 alarm means mounted to said panel member and operatively connected to said flow velocity sensor.

30. The modular display and connection unit described in claim 29, wherein said alarm means comprises:
 means for visually indicating an alarm condition mounted on said front side of said panel member, said means for visually indicating an alarm condition being actuated by a drop in air flow velocity as indicated by said flow velocity sensor.

31. The modular display and connection unit described in claim 30, wherein said means for visually indicating an alarm condition comprises:
 a light emitting diode.

32. A modular display and connection unit for use with a centralized system for removing airborne contaminants from the site of at least one medical procedure being preformed in at least one of a plurality of medical procedure rooms connected to the centralized system, the airborne contaminants being the result of the medical procedures performed in the medical procedure rooms, the centralized system including piping means for transporting the airborne contaminants from the medical procedure room, the modular display and connection unit comprising:
 a panel member having a front side and a rear side, said panel member being mountable to a support assembly providing access to the centralized system for removing airborne contaminants;
 an access outlet integral with said panel member, said access outlet providing access to the centralized system for removing airborne contaminants;
 means for connecting said access outlet to the piping means of the centralized system for removing airborne contaminants; and
 valve control means for controlling the flow of air through said access outlet.

33. The modular display and connection unit described in claim 32, further comprising:
 means for sensing the pressure of air passing through the modular display and connection unit; and
 means for sensing the velocity of air flow through the modular display and connection unit.

34. The modular display and connection unit described in claim 33, further comprising:
 first display means operatively connected to said air pressure sensing means for displaying the pressure of air passing through the modular display and connection unit as detected by said air pressure sensing means, said display means being mountable on said front side of said panel member; and
 second display means operatively connected to said air flow velocity sensing means for displaying the velocity of air flow through the modular display and connection unit as detected by said air flow velocity sensing means, said second display means being mountable on said front side of said panel member.

35. The modular display and connection unit described in claim 34, further comprising:
 first alarm memos mounted to said panel member and operatively connected to said air pressure sensing means; and
 second alarm means mounted to said panel member and operatively connected to said air flow velocity sensing means.

36. The modular display and connection unit described in claim 33, further comprising:
 first alarm means mounted to said panel member and operatively connected to said air pressure sensing means; and
 second alarm means mounted to said panel member and operatively connected to said air flow velocity sensing means.

37. An extension assembly for a medical procedure room for connection to a centralized system for removing airborne contaminants from the site of at least one medical procedure being performed in at least one of a plurality of medical procedure rooms connected to the centralized system, the airborne contaminants being the result of the medical procedures performed in the medical procedure rooms, the centralized system including primary piping means for transporting the airborne contaminants from the medical procedure room, vacuum means connected to the piping means to draw air from the medical procedure room via the primary piping means, and an inlet member permitting access of the extension assembly to the primary piping means, the extension assembly comprising:
 a supplemental piping member extending into the medical procedure room from the inlet member of the centralized system for removing airborne contaminants, said supplemental piping member having a proximal end and a distal end, said distal end of said supplemental piping member being connected to the inlet member;
 support means for properly positioning said supplemental piping member within the medical procedure room; and
 a modular display and connection unit affixed to said support means, said modular display and connection unit including means for connecting to said supplemental piping member.

38. The extension assembly described in claim 37, wherein said supplemental piping member comprises:

smooth-sided, flexible tubing.

39. The extension assembly described in claim 37, wherein said support means comprises:
an articulating arm suspended from the ceiling of the medical procedure room.

40. The extension assembly described in claim 37, wherein said support means comprises:
a medical gas column suspended from the ceiling of the medical procedure room.

41. The extension assembly described in claim 37, wherein said support means comprises:
a wall of the medical procedure room.

42. The extension assembly described in claim 37, wherein said modular display and connection unit comprises:
a panel member having a front side and a rear side;
an access outlet integral with said panel member, said access outlet providing access to the centralized system for removing airborne contaminants;
means for connecting said access outlet to the supplemental piping member of the extension assembly; and
valve control means for controlling the flow of air through said access outlet.

43. The extension assembly described in claim 42, further comprising:
means for sensing the pressure of air passing through the modular display and connection unit; and
means for sensing the velocity of air flow through the modular display and connection unit.

44. The extension assembly described in claim 43, further comprising:
first display means operatively connected to said air pressure sensing means for displaying the pressure of air passing through said modular display and connection unit as detected by said air pressure sensing means, said display means being mountable on said from side of said panel member; and
second display means operatively connected to said air flow velocity sensing means for displaying the velocity of air flow through said modular display and connection unit as detected by said air flow velocity sensing means, said second display means being mountable on said front side of said panel member.

45. The extension assembly described in claim 44, further comprising:
first alarm means mounted to said panel member and operatively connected to said air pressure sensing means; and
second alarm means mounted to said panel member and operatively connected to said air flow velocity sensing means.

46. The extension assembly described in claim 43, further comprising:
first alarm means mounted to said panel member and operatively connected to said air pressure sensing means; and
second alarm means mounted to said panel member and operatively connected to said air flow velocity sensing means.

47. A modular display and connection unit for use with a centralized system for removing airborne contaminants from the site of at least one medical procedure being performed in at least one of a plurality of medical procedure rooms connected to the centralized system, the airborne contaminants being the result of the medical procedures performed in the medical procedure rooms, the centralized system including piping means for transporting the airborne contaminants from the medical procedure room, vacuum means connected to the piping means to draw air from the medical procedure room via the piping means, and a central automated building control system for regulating the vacuum means, the modular display and connection unit comprising:
a panel member having a front side and a rear side, said panel member being mountable to a support assembly providing access to the centralized system for removing airborne contaminants;
an access outlet integral with said panel member, said access outlet providing access to the centralized system for removing airborne contaminants;
means for connecting said access outlet to the piping means of the centralized system for removing airborne contaminants;
means for sensing the pressure of air passing through the modular display and connection unit; and
alarm means operatively connected to said air pressure sensing means and the central automated building control system, whereby upon a drop in air pressure below a predetermined value as detected by said air pressure sensing means, said alarm means transmits a signal to the central automated building control system indicating that the vacuum created by the vacuum means should be increased.

* * * * *

UNITED STATES PATENT AND TRADEMARK OFFICE
CERTIFICATE OF CORRECTION

PATENT NO.  : 5,409,511
DATED       : April 25, 1995
INVENTOR(S) : Gwen A. Paul

It is certified that error appears in the above-indentified patent and that said Letters Patent is hereby corrected as shown below:

In col. 2, line 11, delete "serf" and substitute --self-- therefor.

In col. 2, line 36, delete "aH" and replace with --all--.

In the DESCRIPTION OF THE PREFERRED EMBODIMENT:

In col. 5, line 6, delete "quitable" and substitute --suitable--therefor.

IN col. 6, line 22, delete "aH" and replace with --all--.

In col. 7, line 21, delete "falters" and replace with --filters--.

In col. 8, line 57, delete "falter" and replace with --filter--.

In col. 8, line 58, after the word "treated", delete "falter" and substitute --filter--therefor.

In col. 8, line 63, delete "falter" and replace with --filter--.

In col. 8, line 67, delete "dement" and substitute --element--therefor.

UNITED STATES PATENT AND TRADEMARK OFFICE
CERTIFICATE OF CORRECTION

PATENT NO. : 5,409,511
DATED : April 25, 1995
INVENTOR(S) : Gwen A. Paul

It is certified that error appears in the above-indentified patent and that said Letters Patent is hereby corrected as shown below:

In claim 5, col. 10, line 61, delete "actable" and insert --actuable--therefor.

In claim 35, col. 14, line 24 delete "memos" and replace with --means--.

In claim 44, col. 15, line 41, delete "from" and substitute --front--therefor.

Signed and Sealed this

Twenty-ninth Day of August, 1995

Attest:

BRUCE LEHMAN

Attesting Officer     Commissioner of Patents and Trademarks